(12) United States Patent
Kim et al.

(10) Patent No.: US 9,358,093 B2
(45) Date of Patent: Jun. 7, 2016

(54) BIO-IMPLANTABLE DEVICES HAVING SUPER-HYDROPHOBIC SURFACE AND METHOD FOR MANUFACTURING THEREOF

(71) Applicant: Korea Institute of Science and Technology, Seoul (KR)

(72) Inventors: Soo Hyun Kim, Seoul (KR); Jin Ik Lim, Seoul (KR); Youngmee Jung, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 479 days.

(21) Appl. No.: 13/713,414

(22) Filed: Dec. 13, 2012

(65) Prior Publication Data
US 2014/0012311 A1   Jan. 9, 2014

(30) Foreign Application Priority Data
Jul. 4, 2012 (KR) ................ 10-2012-0072943

(51) Int. Cl.
*A61F 2/01* (2006.01)
*A61L 33/02* (2006.01)

(52) U.S. Cl.
CPC ............. *A61F 2/01* (2013.01); *A61L 33/022* (2013.01); *A61L 2400/12* (2013.01)

(58) Field of Classification Search
CPC ...... A61F 2/01; A61L 33/022; A61L 2400/12
See application file for complete search history.

(56) References Cited

U.S. PATENT DOCUMENTS

| 2011/0171600 A1* | 7/2011 | Yang et al. ............ 433/174 |
| 2012/0074098 A1* | 3/2012 | Nary Filho et al. ........ 216/53 |

* cited by examiner

*Primary Examiner* — Nadine Norton
*Assistant Examiner* — Mahmoud Dahimene
(74) *Attorney, Agent, or Firm* — Goldilocks Zone IP Law

(57) ABSTRACT

The present disclosure relates to a bioimplantable device having a superhydrophobic surface and a method for manufacturing the same. The bioimplantable device, which includes a biocompatible substrate and a superhydrophobic nanostructure formed on the surface of the biocompatible substrate, is capable of preventing blood clot formation by blocking contact with proteins, water, blood platelets, etc. when used for blood vessels.

8 Claims, 1 Drawing Sheet

BIO-IMPLANTABLE DEVICES HAVING SUPER-HYDROPHOBIC SURFACE AND METHOD FOR MANUFACTURING THEREOF

CROSS-REFERENCE TO RELATED APPLICATIONS

This application claims priority under 35 U.S.C. §119 to Korean Patent Application No. 10-2012-0072943 filed on Jul. 4, 2012, in the Korean Intellectual Property Office, the disclosure of which is incorporated herein by reference in its entirety.

TECHNICAL FIELD

The present disclosure relates to a bioimplantable device having a superhydrophobic surface whose surface contacting with blood is made superhydrophobic so as to prevent blood clot formation as much as possible and a method for manufacturing the same.

BACKGROUND

Diseases of the circulatory system including the heart, heart valves and blood vessels are the biggest cause of deaths of adults worldwide. Among them, blood vessel-associated diseases such as arteriosclerosis, angina, myocardial infarction and stroke are the most prevalent.

According to the statistics of the World Health Organization (WHO), it is estimated that about 12 million people die of cardiovascular diseases every year and, in the US, about 57 million people are receiving treatments for one or more cardiovascular diseases. The related cost is reported to amount to 260 billion dollars a year.

Primary therapies for cardiovascular disease include autologous blood vessel implantation or methods of using auxiliary devices for opening the blood vessel such as a stent. Autologous blood vessel implantation is mostly employed in obstructive vascular diseases caused by arteriosclerosis and is often used in genetic fibrosis disorder, aortic aneurysm, aortic dissection, arteritis, aortic injury, etc. Grafts that may be used for autologous blood vessel implantation are very limited such as the internal mammary artery, lumbar artery, ulnar artery, etc. Also, since available vein grafts are limited, autologous blood vessel implantation requiring repeated surgery may be difficult or impossible. Accordingly, to save or improve the quality of life of patients, allogenic blood vessels or artificial blood vessels capable of replacing the autologous blood vessels are required.

At present, artificial blood vessels made of poly(ethylene terephthalate) or polytetrafluoroethylene (PTFE) are used as implantable artificial blood vessels. However, these artificial blood vessels are applicable only to large inner diameters exceeding 6 mm. It is because they can be blocked by small blood clots formed on the inner surface of the blood vessels.

If the blood vessels are narrow with an inner diameter of not greater than 6 mm, even small blood clots may block the blood vessels and lead to fatal results. To solve this problem, blood clot formation on the inside wall of the blood vessel should be prevented. Associated methods include a tissue engineering method of inoculating ordinary cells or stem cells to a biodegradable, blood vessel-shaped support and growing the cells, a method of attaching only the vascular endothelial cells that prevent blood clot formation on the inner surface of a biodegradable or non-degradable support, or a method of attaching heparin, warfarin or a negatively charged functional group without using cells. However, the method using vascular endothelial cells has difficulty in that the handling of the vascular endothelial cells is not easy. And, although the method of using heparin, etc. is somewhat effective in the early stage, blood clots are formed with time. Accordingly, the need on new practical materials capable of replacing blood vessels is ever increasing.

Meanwhile, stainless steel or titanium alloy is frequently used to make a stent. If the blood vessel wall is damaged by such material, smooth muscle cells may grow at the wound site and block the blood vessel. Also, blood platelets tend to aggregate on the surface of the material, thus forming blood clots and blocking the blood vessel. In order to prevent such unwanted tissue capsulation or blood clotting, negatively charged functional groups are attached on the surface of the stent or drugs such as cyclosporin A are used. However, these methods are problematic in that the blood vessel is blocked again as time goes by.

Korean Patent No. 0661396 discloses an anti-thrombogenic stent coated with multiple layers in which hydrophobic heparin polymers are distributed in the upper layer. The stent is applicable to blood vessels with large inner diameters but not to those with small inner diameters. In addition, since it exhibits weak hydrophobicity, proteins, blood platelets, etc. may be easily attached to the surface of the stent through hydrophobic interaction.

Accordingly, an artificial blood vessel or a stent which is applicable to blood vessels with small and large inner diameters and is capable of minimizing blood clot formation is needed.

SUMMARY

The present disclosure is directed to providing a bioimplantable device having a superhydrophobic surface on the side where blood comes into contact and thus capable of preventing blood clot formation on the surface of the bioimplantable device.

The present disclosure is also directed to providing a method for manufacturing the bioimplantable device having a superhydrophobic surface.

An anti-thrombogenic bioimplantable device having a superhydrophobic surface according to the present disclosure may include: a biocompatible substrate; and a superhydrophobic nanostructure formed on the surface of the biocompatible substrate.

The anti-thrombogenic bioimplantable device may have a superhydrophobic surface with a water contact angle of 150° or greater.

In an exemplary embodiment of the present disclosure, the biocompatible substrate may be a biocompatible polymer film or a metal wire coated with a biocompatible polymer. The polymer of the biocompatible substrate may be selected from a group consisting of polylactide, polycaprolactone, polyglycolide, polypropylene, polyethylene, polyvinyl chloride, polybutadiene, poly(methyl methacrylate), poly(acrylic acid), poly(2-hydroxyethlymethacrylate), polycarbonate, poly(ethylene terephthalate), polyurethane and blends or copolymers thereof.

The nanostructure may be formed of anodized aluminum oxide or magnesium oxide.

A method for manufacturing an anti-thrombogenic bioimplantable device having a superhydrophobic surface according to the present disclosure may include: (a) forming a nanoporous metal oxide film on the surface of a biocompatible substrate; (b) forming a nanostructure on the biocompatible substrate by subjecting the biocompatible substrate having the nanoporous metal oxide film formed to a pseudo-vacuum state of 60-250° C.; (c) removing the nanoporous metal oxide film remaining on the portion where the nanostructure is not formed by treating the biocompatible substrate having the nanostructure formed with a metal oxide film removing solution; and (d) washing the biocompatible substrate having the nanoporous metal oxide film removed with alcohol and distilled water and then drying.

The method may further comprise, before the step (a) of forming the nanoporous metal oxide film, applying one or more solvent selected from a group consisting of chloroform, acetone, tetrahydrofuran, toluene, xylene and dioxane on the surface of the biocompatible substrate. The solvent may be applied on the surface of the biocompatible substrate in an amount of 1-1000 μL per 10 mm².

In the step (a), the biocompatible substrate may be a biocompatible polymer film or a metal wire coated with a biocompatible polymer.

In the step (a), the polymer of the biocompatible substrate may be selected from a group consisting of polylactide, polycaprolactone, polyglycolide, polypropylene, polyethylene, polyvinyl chloride, polybutadiene, poly(methyl methacrylate), poly(acrylic acid), poly(2-hydroxyethlymethacrylate), polycarbonate, poly(ethylene terephthalate), polyurethane and blends or copolymers thereof.

The metal wire may be formed of one selected from a group consisting of aluminum, stainless steel, iron, nickel, copper, silver, gold, titanium, zirconium and alloys thereof.

In the step (a), the nanoporous metal oxide film may have pores with an average diameter of 20-500 nm. Specifically, the nanoporous metal oxide film may include anodized aluminum oxide or magnesium oxide.

In the step (b), the pressure of the pseudo-vacuum state may be 0.01-0.5 MPa.

In the step (c), the metal oxide film removing solution may be one selected from a group consisting of an aqueous hydrogen peroxide ($H_2O_2$) solution, an aqueous sodium hydroxide (NaOH) solution, an aqueous potassium hydroxide (KOH) solution and mixture solutions thereof.

Since the bioimplantable device of the present disclosure has superior superhydrophobicity with a water contact angle of 150° or greater, it can minimize blood clot formation by blocking contact with proteins, water, blood platelets, etc. when used for blood vessels and the effect lasts long.

Whereas the existing bioimplantable device is applicable only to blood vessels having large inner diameters, the bioimplantable device of the present disclosure is applicable to blood vessels having small inner diameters of 6 mm or smaller as well as those with large inner diameters.

In addition, since the bioimplantable device of the present disclosure is stable against cells, it can be readily used without the stabilization procedure of incubating for a long time with cells.

BRIEF DESCRIPTION OF THE DRAWING

The above and other objects, features and advantages of the present disclosure will become apparent from the following description of certain exemplary embodiments given in conjunction with the accompanying drawing, in which:

FIG. 1 is a photograph of a bioimplantable device manufactured according to an embodiment of the present disclosure.

DETAILED DESCRIPTION OF EMBODIMENTS

The present disclosure relates to a bioimplantable device having a superhydrophobic surface, capable of preventing blood clot formation by blocking contact with proteins, water, blood platelets, etc., and a method for manufacturing the same.

Hereinafter, exemplary embodiments will be described in detail with reference to the accompanying drawing.

An anti-thrombogenic bioimplantable device having a superhydrophobic surface according to the present disclosure comprises: a biocompatible substrate; and a superhydrophobic nanostructure formed on the surface of the biocompatible substrate.

The biocompatible substrate may comprise a material resulting in no adverse effects when used for example, for blood vessels. Specifically, a polymer selected from a group consisting of polylactide, polycaprolactone, polyglycolide, polypropylene, polyethylene, polyvinyl chloride, polybutadiene, poly(methyl methacrylate), poly(acrylic acid), poly(2-hydroxyethlymethacrylate), polycarbonate, poly(ethylene terephthalate), polyurethane and blends or copolymers thereof may be used. More specifically, polylactide, polycaprolactone and blends or copolymers thereof may be used.

The superhydrophobic nanostructure may comprise a nanoporous metal oxide film, e.g. anodized aluminum oxide or magnesium oxide.

The bioimplantable device of the present disclosure has a water contact angle of 150° or greater, preferably 165-175°.

The present disclosure also provides a method for manufacturing an anti-thrombogenic bioimplantable device having a superhydrophobic surface.

The method for manufacturing an anti-thrombogenic bioimplantable device having a superhydrophobic surface according to the present disclosure comprises: (a) forming a nanoporous metal oxide film on the surface of a biocompatible substrate; (b) forming a nanostructure on the biocompatible substrate having the nanoporous metal oxide film formed; (c) removing the nanoporous metal oxide film remaining on the portion where the nanostructure is not formed; and (d) washing the biocompatible substrate having the nanoporous metal oxide film removed with alcohol and distilled water and then drying.

First, in the step (a), a nanoporous metal oxide film is formed to come in contact with the surface of a biocompatible substrate.

The biocompatible substrate may be in the form of a biocompatible polymer film or a metal wire coated with a biocompatible polymer.

If the biocompatible polymer film has a planar shape, the nanoporous metal oxide film is formed on the upper side of the polymer film and, if the biocompatible polymer film has a cylindrical shape, the nanoporous metal oxide film is inserted in the cylindrical polymer film. If the biocompatible substrate is a cylindrical metal wire coated (on the inner side of the metal wire) with a biocompatible polymer, the nanoporous metal oxide film is inserted in the cylindrical metal wire.

The metal wire on which the biocompatible polymer is coated may comprise one selected from a group consisting of aluminum, stainless steel, iron, nickel, copper, silver, gold, titanium, zirconium and alloys thereof. A bioimplantable device comprising the wire having a superhydrophobic surface may be used as a stent.

The nanoporous metal oxide film may comprise anodized aluminum oxide or magnesium oxide having a plurality of pores with an average diameter of 20-500 nm, specifically 100-300 nm. If the average diameter is smaller than the lowest limit, high temperature and pressure are required to form the structure of a regular size on the surface of the bioimplantable device, which may cause stability problem of the bioimplantable device. And, if the average diameter is larger than the highest limit, the structure formed on the bioimplantable device has an increased size, resulting in decreased water contact angle and decreased superhydrophobicity.

When ordinary, unanodized metal film is used as the nanoporous metal oxide film, adhesion with the biocompatible substrate decreases and the cost for preparing a uniform nano/micro-sized porous metal film increases greatly. In addition, harsh conditions such as high heat and pressure and strong acid or base are required to remove the metal film in the following step, which deteriorates durability of the bioimplantable device against continuously flowing blood.

To provide a superhydrophobic surface under a milder condition, one or more solvent selected from a group consisting of chloroform, acetone, tetrahydrofuran, toluene, xylene and dioxane may be applied on the surface of the biocompatible substrate before forming the nanoporous metal oxide film on the biocompatible substrate. That is to say, the nanoporous metal oxide film is formed after the solvent is applied on the surface of the biocompatible substrate. When the solvent is applied on the surface of the biocompatible substrate, a solution of the biocompatible substrate slightly dissolved in the solvent fills the pores of the nanoporous metal oxide film through capillary action. As a result, the solution fills the nanostructure. The solvent is evaporated upon natural drying and, after the nanoporous metal oxide film is removed in the step (c), a nanostructure is formed on the surface of the biocompatible substrate. In addition, the application of the solvent further improves superhydrophobicity and improves stability and durability of the bioimplantable device, while allowing processing under mild conditions.

The solvent is applied on the surface of the biocompatible substrate in an amount of 1-1000 µL, specifically 500-900 µL, per 10 mm$^2$. When the amount of the solvent applied on the surface of the biocompatible substrate is smaller than the lowest limit, the nanostructure may not be formed as desired due to insufficient capillary action, resulting in decreased superhydrophobicity. And, if the amount of the solvent applied on the surface of the biocompatible substrate is larger than the highest limit, the solvent may overflow to the surface of the nanoporous metal oxide film, making it unable to remove the nanoporous metal oxide film and resulting in decreased superhydrophobicity.

Next, in the step (b), the nanostructure is formed on the biocompatible substrate having the nanoporous metal oxide film formed.

The biocompatible substrate having the nanoporous metal oxide film formed is subjected to a pseudo-vacuum state (0.01-0.5 MPa) of 60-250° C., specifically 150-250° C., for 1-24 hours, specifically 12-24 hours, to form the nanostructure on the surface of the biocompatible substrate.

If the temperature is below the lowest limit when forming the nanostructure, the nanostructure may not be formed due to insufficient fluidity on the surface of the biocompatible substrate. And, if the temperature is above the highest limit, thermal loss may occur due to, for example, pyrolysis of the biocompatible substrate and superhydrophobicity may not be attained because the nanoporous metal oxide film is modified.

And, if the time for forming the nanostructure is shorter than the lowest limit, superior superhydrophobicity may not be attained because the biocompatible substrate (or the solution of the biocompatible substrate slightly dissolved in the solvent) fails to penetrate sufficiently into the pores of the nanoporous metal oxide film. And, if the time is longer than the highest limit, the biocompatible substrate may be thermally degraded and superhydrophobicity may not be attained because the nanoporous metal oxide film is modified.

Next, in the step (c), the nanoporous metal oxide film remaining on the portion of the biocompatible substrate where the nanostructure is not formed in the step (b) is removed by treating with a metal oxide film removing solution for 2-5 hours.

The metal oxide film removing solution may be one selected from a group consisting of an aqueous hydrogen peroxide ($H_2O_2$) solution, an aqueous sodium hydroxide (NaOH) solution, an aqueous potassium hydroxide (KOH) solution and mixture solutions thereof, specifically an aqueous sodium hydroxide solution.

Next, in the step (d), the biocompatible substrate having the nanoporous metal oxide film removed is washed sequentially with alcohol and distilled water for 1-3 hours, and then dried.

The biocompatible substrate having the nanoporous metal oxide film removed should be washed with alcohol and distilled water for at least 5 times in order to obtain a bioimplantable device without impurities.

The drying may be performed by natural drying or freeze-drying. Specifically, freeze-drying may be formed at −10 to −100° C. for 10-30 hours.

To be applicable to blood vessels, the bioimplantable device of the present disclosure may be prepared into a cylindrical shape (see FIG. 1). After the bioimplantable device is manufactured as a planar film, it may be prepared into a cylindrical shape by using an adhesive such as fibrin glue such that the superhydrophobic surface faces inward.

The film-type bioimplantable device may be used as artificial blood vessel, and the bioimplantable device manufactured using the metal wire may be used as a stent.

The examples and experiments will now be described. The following examples and experiments are for illustrative purposes only and not intended to limit the scope of this disclosure.

EXAMPLE 1

10 mL of a mixture solution of 10 wt % of polylactide (poly-L-lactide; PLLA) and 90 wt % of chloroform was added to a Teflon mold (40×40 mm) and dried for 2 weeks under normal temperature and normal pressure to prepare a PLLA film. An aluminum oxide film having pores with an average diameter of 200 nm was placed on the prepared PLLA film and subjected to a pseudo-vacuum state of 0.1 MPa at 200° C. for 12 hours so as to form a nanostructure on the surface of the PLLA film. Thereafter, the PLLA film having the nanostructure formed was put in a 5 M aqueous sodium hydroxide solution and shaken for 3 hours to remove the aluminum oxide film. After washing 3 times with ethanol, for 1 hour each, and 5 times with distilled water, for 1 hour each, the washed PLLA film was dried at −78° C. for 20 hours to obtain a bioimplantable device.

EXAMPLE 2

A bioimplantable device was manufactured in the same manner as in Example 1, except for using 15 wt % of polylactide-co-caprolactone (poly-L-lactide-co-caprolactone; PLCL, 50:50) instead of 10 wt % of polylactide and subjecting to a pseudo-vacuum state of 0.2 MPa at 150° C. for 24 hours.

EXAMPLE 3

10 mL of a mixture solution of 10 wt % of polylactide-co-caprolactone (poly-L-lactide-co-caprolactone; PLCL, 50:50) and 90 wt % of chloroform was dip-coated onto a Teflon rod mold (inner diameter=4 mm, length=40 mm) and dried for 3 weeks under normal temperature and normal pressure while rotating at 10 rpm to prepare a cylindrical PLLA film. An aluminum oxide film having pores with an average diameter of 200 nm was inserted in the prepared PLLA film and subjected to a pseudo-vacuum state of 0.1 MPa at 180° C. for 24 hours so as to form a nanostructure on the surface of the PLLA film. Thereafter, a bioimplantable device was manufactured in the same manner as in Example 1.

EXAMPLE 4

A bioimplantable device was manufactured in the same manner as in Example 3, except for applying 1000 μL of dioxane on the inner side of the cylindrical PLCL film per 10 mm² of the film before inserting the aluminum oxide film.

EXAMPLE 5

10 mL of a mixture solution of 15 wt % of polylactide (poly-L-lactide; PLLA) and 85 wt % of chloroform was coated onto nickel-titanium alloy (20×20×0.3 mm) and naturally dried for 3 weeks. After applying 500 μL of dioxane on the coated surface per 10 mm² of the surface, an aluminum oxide film having pores with an average diameter of 200 nm was inserted and subjected to a pseudo-vacuum state of 0.1 MPa at 180° C. for 24 hours so as to form a nanostructure on the coated PLLA surface. Thereafter, a bioimplantable device was manufactured in the same manner as in Example 1.

COMPARATIVE EXAMPLE 1

A bioimplantable device was manufactured in the same manner as in Example 1, except for using polystyrene instead of polylactide.

TEST EXAMPLE 1

Measurement of Water Contact Angle

The contact angle between the surface of the bioimplantable devices manufactured in Examples 1-5 and Comparative Example 1 and a water drop was measured using a contact angle meter (Phoenix 150; Surface Electro Optics, Seoul, Korea). The result is shown in Table 1.

TABLE 1

| | Example 1 | Example 2 | Example 3 | Example 4 | Example 5 | Comparative Example 1 |
|---|---|---|---|---|---|---|
| Angle (°) | 165 | 170 | 170 | 174 | 170 | 140 |

As seen from Table 1, the bioimplantable devices manufactured in Examples 1-3 according to the present disclosure showed superhydrophobicity with water contact angles of 165° or greater. In general, a surface with a water contact angle of 150° or greater is called superhydrophobic and one with a water contact angle of 60° or greater is called hydrophobic.

The bioimplantable devices manufactured by applying the solvent to the biocompatible substrate in Examples 4-5 showed better superhydrophobicity than those wherein the solvent was not used.

In contrast, the bioimplantable device manufactured using polystyrene in Comparative Example 1 showed hydrophobicity, not superhydrophobicity.

TEST EXAMPLE 2

Cytotoxicity Test

The bioimplantable devices manufactured in Examples 1-5 and Comparative Example 1 were added to a Petri dish containing a confluent layer of cells. 24 hours later, the cytotoxic effect on the cells was evaluated with scores from 0 to 5 as follows. The result is shown in Table 2.

0: No cytotoxic effect (No cells were killed.)
1: Not more than 10% of the cells were killed.
2: Not more than 25% of the cells were killed.
3: Not more than 50% of the cells were killed.
4: Not more than 85% of the cells were killed.
5: All the cells were killed.

TABLE 2

| | Example 1 | Example 2 | Example 3 | Example 4 | Example 5 | Comparative Example 1 |
|---|---|---|---|---|---|---|
| Cytotoxicity | 0 | 0 | 0 | 0 | 0 | 2 |

As seen from Table 2, since the bioimplantable devices manufactured in Examples 1-3 according to the present disclosure showed no cytotoxicity, they can be readily used as artificial blood vessel or stent. Also, the bioimplantable devices manufactured using the solvent in Examples 4-5 showed no cytotoxicity.

In contrast, since the bioimplantable device manufactured using polystyrene in Comparative Example 1 showed cytotoxicity, it is not applicable as artificial blood vessel or stent. In addition, it was found that the bioimplantable device manufactured in Comparative Example 1 suffers degraded durability when brought into contact with blood.

While the present disclosure has been described with respect to the specific embodiments, it will be apparent to those skilled in the art that various changes and modifications may be made without departing from the spirit and scope of the disclosure as defined in the following claims.

What is claimed is:
1. A method for manufacturing an anti-thrombogenic bioimplantable device having a superhydrophobic surface, comprising:
   forming a nanoporous metal oxide film on the surface of a biocompatible substrate;
   forming a nanostructure on the biocompatible substrate by subjecting the biocompatible substrate having the nanoporous metal oxide film formed to a temperature of 60-250° C. and the pressure of 0.01-0.5 Mpa;
   removing the nanoporous metal oxide film remaining on the portion where the nanostructure is not formed by treating the biocompatible substrate having the nanostructure formed with a metal oxide film removing solution; and
   washing the biocompatible substrate having the nanoporous metal oxide film removed with alcohol and distilled water and then drying,
   wherein before said forming the nanoporous metal oxide film, applying one or more solvent selected from a group consisting of chloroform, acetone, tetrahydrofuran, toluene, xylene and dioxane on the surface of the biocompatible substrate.

2. The method for manufacturing an anti-thrombogenic bioimplantable device having a superhydrophobic surface according to claim 1, wherein the solvent is applied on the surface of the biocompatible substrate in an amount of 1-1000 μL per 10 mm$^2$.

3. The method for manufacturing an anti-thrombogenic bioimplantable device having a superhydrophobic surface according to claim 1, wherein, in said forming the nanoporous metal oxide film, the biocompatible substrate is a biocompatible polymer film or a metal wire coated with a biocompatible polymer.

4. The method for manufacturing an anti-thrombogenic bioimplantable device having a superhydrophobic surface according to claim 1, wherein, in said forming the nanoporous metal oxide film, the biocompatible substrate comprises a polymer selected from a group consisting of polylactide, polycaprolactone, polyglycolide, polypropylene, polyethylene, polyvinyl chloride, polybutadiene, poly(methyl methacrylate), poly(acrylic acid), poly(2-hydroxyethlymethacrylate), polycarbonate, poly(ethylene terephthalate), polyurethane and blends or copolymers thereof.

5. The method for manufacturing an anti-thrombogenic bioimplantable device having a superhydrophobic surface according to claim 3, wherein the metal wire comprises one selected from a group consisting of aluminum, stainless steel, iron, nickel, copper, silver, gold, titanium, zirconium and alloys thereof.

6. The method for manufacturing an anti-thrombogenic bioimplantable device having a superhydrophobic surface according to claim 1, wherein, in said forming the nanoporous metal oxide film, the nanoporous metal oxide film has pores with an average diameter of 20-500 nm.

7. The method for manufacturing an anti-thrombogenic bioimplantable device having a superhydrophobic surface according to claim 1, wherein, in said forming the nanoporous metal oxide film, the nanoporous metal oxide film comprises anodized aluminum oxide or magnesium oxide.

8. The method for manufacturing an anti-thrombogenic bioimplantable device having a superhydrophobic surface according to claim 1, wherein, in said removing the nanoporous metal oxide film remaining on the portion where the nanostructure is not formed, the metal oxide film removing solution is one selected from a group consisting of an aqueous hydrogen peroxide ($H_2O_2$) solution, an aqueous sodium hydroxide (NaOH) solution, an aqueous potassium hydroxide (KOH) solution and mixture solutions thereof.

\* \* \* \* \*